US011923089B2

(12) United States Patent
Yamazaki et al.

(10) Patent No.: US 11,923,089 B2
(45) Date of Patent: Mar. 5, 2024

(54) DIAGNOSIS SUPPORTING SYSTEM, DIAGNOSIS SUPPORTING APPARATUS, AND DIAGNOSIS SUPPORTING METHOD

(71) Applicant: CANON MEDICAL SYSTEMS CORPORATION, Otawara (JP)

(72) Inventors: Yudai Yamazaki, Nasushiobara (JP); Longxun Piao, Nasushiobara (JP); Yuka Shimomura, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 465 days.

(21) Appl. No.: 17/062,920

(22) Filed: Oct. 5, 2020

(65) Prior Publication Data
US 2021/0104324 A1 Apr. 8, 2021

(30) Foreign Application Priority Data

Oct. 3, 2019 (JP) .................................. 2019-182726

(51) Int. Cl.
*G16H 50/20* (2018.01)
*G16H 10/60* (2018.01)
(Continued)

(52) U.S. Cl.
CPC ............. *G16H 50/20* (2018.01); *G16H 10/60* (2018.01); *G16H 15/00* (2018.01); *G16H 50/30* (2018.01)

(58) Field of Classification Search
CPC ........ G16H 10/60; G16H 15/00; G16H 50/20; G16H 50/30; G06Q 50/22; G06Q 50/24;
(Continued)

(56) References Cited

U.S. PATENT DOCUMENTS

2004/0073121 A1 4/2004 Sun
2007/0136015 A1* 6/2007 Suzuki ............... G05B 23/0232
370/241
(Continued)

FOREIGN PATENT DOCUMENTS

JP 2004-154564 A 6/2004
JP 2014-194712 A 10/2014
(Continued)

OTHER PUBLICATIONS

Japanese Office Action dated Jul. 25, 2023, in Japanese Patent Application No. 2019-182726, 4 pages.

*Primary Examiner* — Mamon Obeid
*Assistant Examiner* — Alaaeldin M Elshaer
(74) *Attorney, Agent, or Firm* — Oblon, McClelland, Maier & Neustadt, L.L.P.

(57) ABSTRACT

A diagnosis supporting system according to embodiments includes a memory that stores medical information including patient information relating to a condition of a patient, and intervention information relating to an intervention for the patient; and processing circuitry that extracts a change point in the medical information, that calculates a first change amount indicating a change in the patient information between before and after the change point, and a second change amount indicating a change in the intervention information between before and after the change point, and that performs display based on the first change amount and the second change amount in a display mode set according to at least one of the first change amount and the second change amount.

13 Claims, 15 Drawing Sheets

(51) Int. Cl.
  *G16H 15/00*   (2018.01)
  *G16H 50/30*   (2018.01)

(58) Field of Classification Search
  CPC ........... A61B 5/00; A61B 5/0245; A61B 5/08;
       A61B 5/087; G08B 24/04; A61G 12/00;
       G01R 29/02; G06N 3/08
  USPC ........................................................ 705/2, 3
  See application file for complete search history.

(56) References Cited

U.S. PATENT DOCUMENTS

| | | | |
|---|---|---|---|
| 2015/0371419 | A1 | 12/2015 | Hoshino |
| 2017/0017764 | A1* | 1/2017 | Tsugo .................... G16H 40/63 |
| 2017/0238867 | A1* | 8/2017 | Javed ....................... A61B 5/08 |
| 2020/0029832 | A1 | 1/2020 | Kogure |

FOREIGN PATENT DOCUMENTS

| | | | | |
|---|---|---|---|---|
| JP | 2015-197737 | A | | 11/2015 |
| JP | 2016-171907 | A | | 9/2016 |
| JP | 2018000232 | A | * | 1/2018 |
| JP | 2019-097828 | A | | 6/2019 |
| WO | WO 2014/006862 | A1 | | 1/2014 |
| WO | WO-2018051343 | A1 | * | 3/2018 |

\* cited by examiner

INTERVENTION INFORMATION

| | 2019.5.17 | 2019.5.18 | 2019.5.19 | 2019.5.20 | 2019.5.21 | 2019.5.22 | 2019.5.23 | 2019.5.24 |
|---|---|---|---|---|---|---|---|---|
| DIURETIC DRUG | | 10 | 10 | | 10 | | | |
| CARDIOTONIC DRUG | | | 20 | | | | | |

PATIENT INFORMATION

| | 2019.5.17 | 2019.5.18 | 2019.5.19 | 2019.5.20 | 2019.5.21 | 2019.5.22 | 2019.5.23 | 2019.5.24 |
|---|---|---|---|---|---|---|---|---|
| NT-proBNP | 192 | 185 | 200 | 180 | 92 | 100 | 89 | 102 |
| RESPIRATION RATE | 8 | 12 | 14 | 13 | 23 | 21 | 20 | 19 |

FIG.6

| | 2019.5.17 | 2019.5.18 | 2019.5.19 | 2019.5.20 | 2019.5.21 | 2019.5.22 | 2019.5.23 | 2019.5.24 |
|---|---|---|---|---|---|---|---|---|
| DIURETIC DRUG | | 10 | 10 | | 10 | | | |
| CARDIOTONIC DRUG | | | 20 | | | | | |
| NT-proBNP | 192 | 185 | 200 | 180 | 92 | 100 | 89 | 102 |
| RESPIRATION RATE | 8 | 12 | 14 | 13 | 23 | 21 | 20 | 19 |

R11 — R12

⇧ CHANGE POINT V1

FIG.7

| | 2019.5.17 | 2019.5.18 | 2019.5.19 | 2019.5.20 | 2019.5.21 | 2019.5.22 | 2019.5.23 | 2019.5.24 |
|---|---|---|---|---|---|---|---|---|
| DIURETIC DRUG | | 10 | 10 | | 10 | | | |
| CARDIOTONIC DRUG | | | 20 | | | | | |
| NT-proBNP | 192 | 185 | 200 | 180 | 92 | 100 | 89 | 102 |
| RESPIRATION RATE | 8 | 12 | 14 | 13 | 23 | 21 | 20 | 19 |

CHANGE POINT V2, R21, CHANGE POINT V1, R22, CHANGE POINT V3

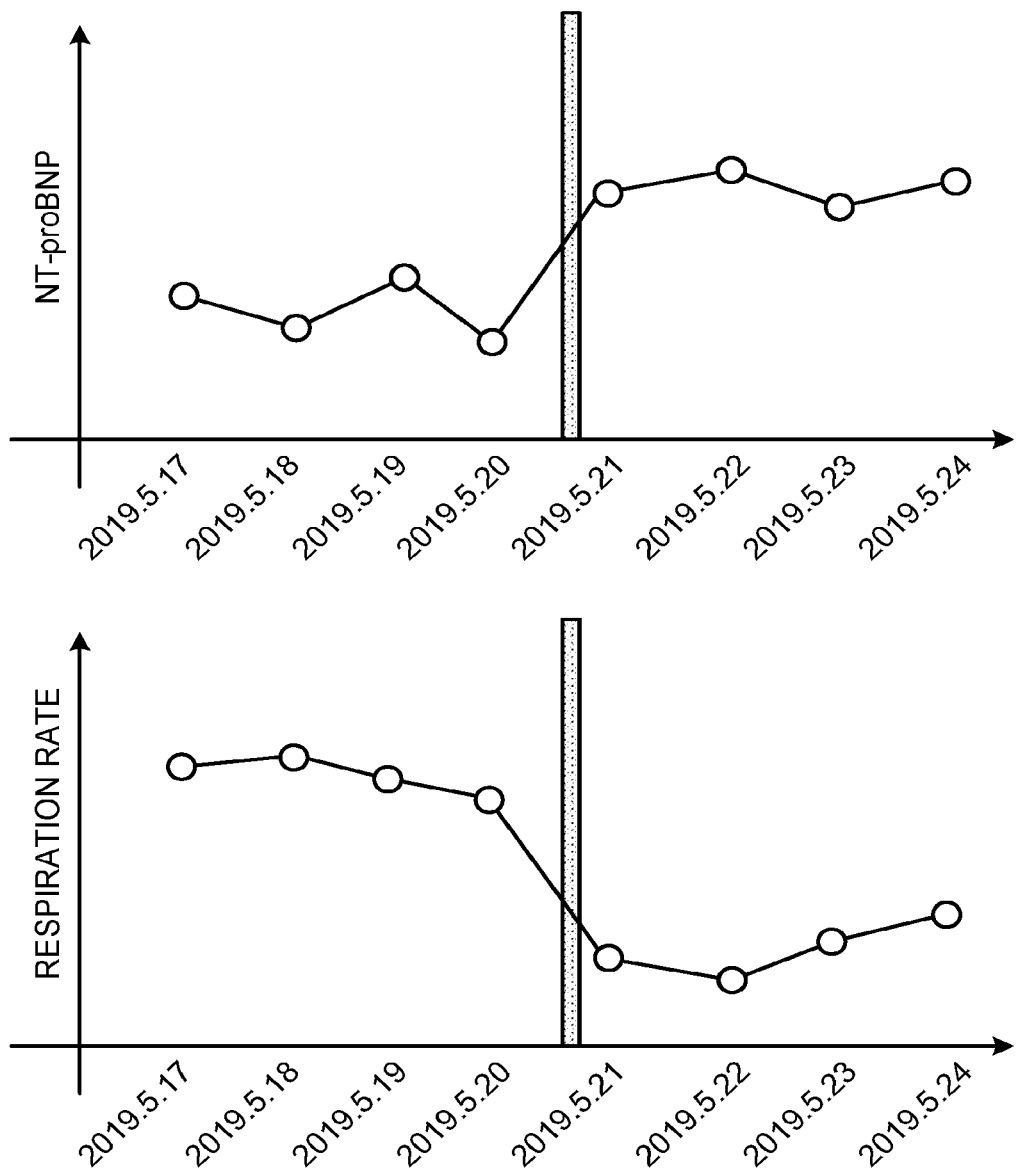

FIG.11D

| | 2019.5.17 | 2019.5.18 | 2019.5.19 | 2019.5.20 | 2019.5.21 | 2019.5.22 | 2019.5.23 | 2019.5.24 |
|---|---|---|---|---|---|---|---|---|
| DIURETIC DRUG | | 10 | 10 | | 10 | | | |
| CARDIOTONIC DRUG | | | 20 | | | | | |
| NT-proBNP | 192 | 185 | 200 | 180 | 92 | 100 | 89 | 102 |
| RESPIRATION RATE | 8 | 12 | 14 | 13 | 23 | 21 | 20 | 19 |

FIG.13

| PRIORITY | INTERVEN-TION CHANGE DEGREE | CONDITION CHANGE DEGREE | CHANGE POINT | BEFORE CHANGE | AFTER CHANGE |
|---|---|---|---|---|---|
| 1 | 0.9 | 0.1 | 2019.5.20 23:34:24 | CARDIOTONIC DRUG: 20 RESPIRATION RATE: 22 | CARDIOTONIC DRUG: 3 RESPIRATION RATE: 21 |
| 2 | 0.8 | 0.2 | 2019.5.19 08:54:23 | BLOOD PRESSURE: 190 DIURETIC DRUG: 10 | BLOOD PRESSURE: 120 DIURETIC DRUG: 20 |
| 3 | 0.2 | 0.2 | 2019.5.23 12:12:11 | CARDIOTONIC DRUG: 10 | CARDIOTONIC DRUG: 30 |
| 4 | 0.1 | 0.6 | 2019.5.20 11:12:11 | ... | ... |
| 5 | 0.1 | 0.7 | 2019.5.21 14:43:21 | ... | ... |
| 6 | 0.2 | 0.9 | 2019.5.17 11:32:43 | ... | ... |

US 11,923,089 B2

DIAGNOSIS SUPPORTING SYSTEM, DIAGNOSIS SUPPORTING APPARATUS, AND DIAGNOSIS SUPPORTING METHOD

CROSS-REFERENCE TO RELATED APPLICATIONS

This application is based upon and claims the benefit of priority from Japanese Patent Application No. 2019-182726, filed on Oct. 3, 2019; the entire contents of which are incorporated herein by reference.

FIELD

Embodiments described herein relate generally to a diagnosis supporting system, a diagnosis supporting apparatus, and a diagnosis supporting method.

BACKGROUND

Medical doctors perform various kinds of decision making based on past examination information and treatment information of a patient, and various other medical information about the patient. However, there is a case in which an enormous amount of medical information is recorded depending on a patient, and it is difficult to be aware of all the information.

BRIEF DESCRIPTION OF THE DRAWINGS

FIG. 6 is a diagram illustrating an example of extraction processing of a first period and a second period according to the first embodiment;

FIG. 7 is a diagram illustrating an example of the extraction processing of the first period and the second period according to the first embodiment;

FIG. 11A is a diagram illustrating a display example according to the first embodiment;

FIG. 11D is a diagram illustrating a display example according to the first embodiment;

FIG. 13 is a diagram illustrating a display example according to a second embodiment.

DETAILED DESCRIPTION

Hereinafter, embodiments of a diagnosis supporting system, a diagnosis supporting apparatus, and a diagnosis supporting method will be explained in detail with reference to the accompanying drawings. The embodiments described below are not intended to limit the diagnosis supporting system, the diagnosis supporting apparatus, and the diagnosis supporting method.

First, a first embodiment will be explained. In the first embodiment, a diagnosis supporting system 1 that includes a diagnosis supporting apparatus 10 and a database 20 will be explained.

Figure 1:
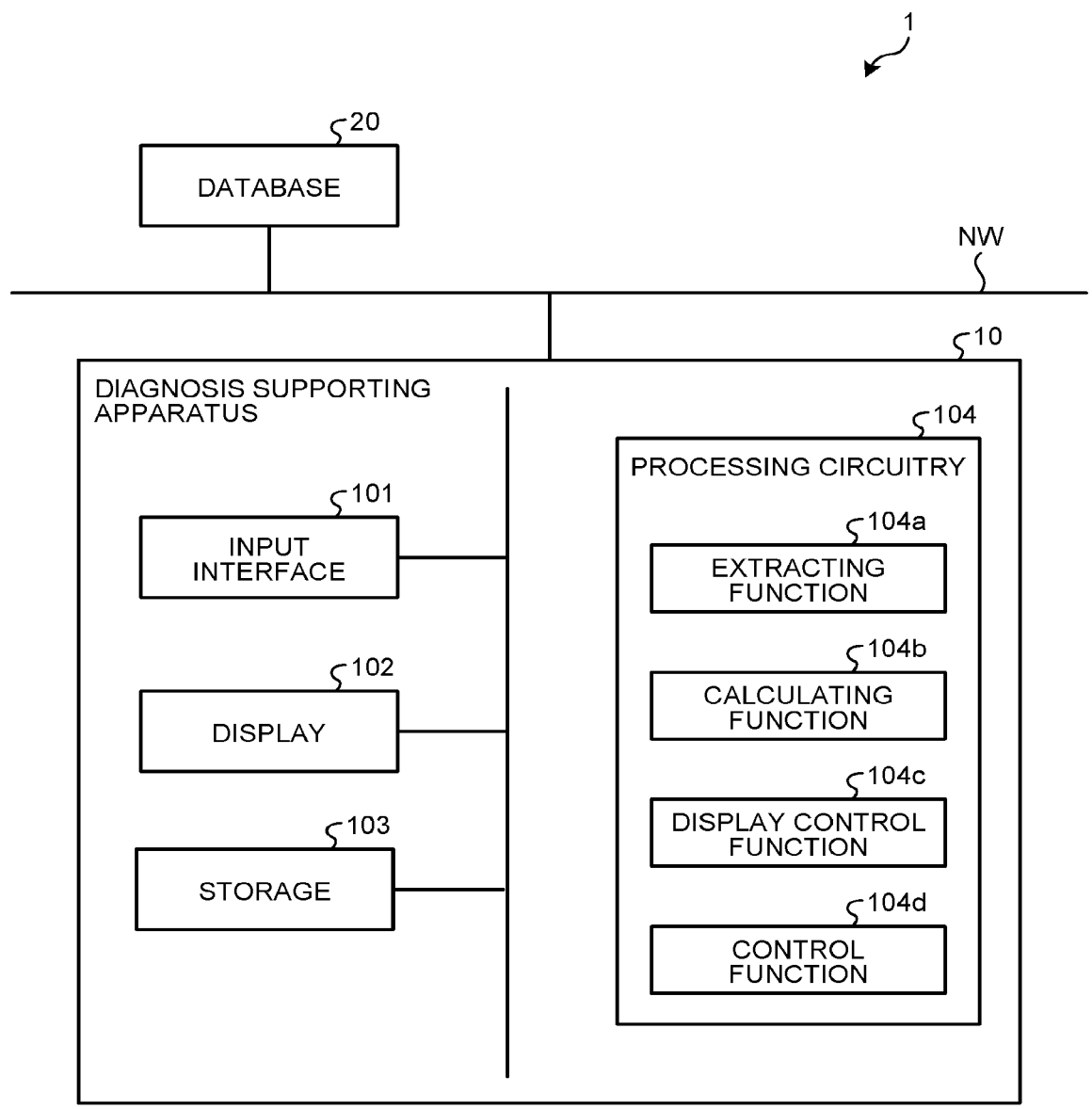
FIG. 1 is a block diagram illustrating an example of a system configuration of a diagnosis supporting system according to a first embodiment.

FIG. 1 is a block diagram illustrating an example of a configuration of the diagnosis supporting system 1 according to the first embodiment. As illustrated in FIG. 1, the diagnosis supporting system 1 according to the first embodiment includes the diagnosis supporting apparatus 10 and the database 20. Moreover, as illustrated in FIG. 1, the diagnosis supporting apparatus 10 and the database 20 are connected to each other through a network NW.

The database 20 is a storage device that stores medical information about a patient. The database 20 is one example of a storage unit (a memory).

As one example, the database 20 is an electronic-medical-chart storage device that is installed as a part of an electronic medical-chart system introduced in a hospital or the like. Furthermore, as one example, the database 20 is a general management apparatus that acquires various kinds of medical information from various kinds of medical information systems, such as an electronic medical-chart system, a picture archiving and communication system (PACS), a radiation department system, and a specimen examination system, and that manages the acquired medical information as a platform. Although the database 20 is illustrated as a single unit in FIG. 1, the database 20 may be constituted of plural physically separated storage devices in a combined manner. Moreover, these plural storage devices may be installed in different facilities from each other.

The medical information about a patient includes patient information about a condition of the patient, and intervention information about intervention for the patient. For example, the database 20 stores various kinds of medical information, associating with information of time and date on which the medical information is acquired and a patient ID.

For example, the patient information includes examination information collected from examinations. Specifically, examples of the examination information include measured vital data of a patient (for example, a pulse rate, a heart rate, a respiration rate, a blood pressure, a body temperature, a percutaneous oxygen saturation (SpO2), and the like), examination data of a specimen (blood and the like) collected from the patient, medical image data collected from the patient, measurement data of medical image data (a blood vessel diameter, a blood flow volume, and the like), and the like. In addition, the patient information includes various kinds of information about a condition of the patient, such as a meal size, a voided volume, and a symptom described by the patient (pain, itchiness, and the like).

Moreover, the intervention information includes for example, treatment information about a treatment given to the patient. Specifically, examples of the treatment information include information about a medicine given to the patient (a kind and an amount of medicine applied, and the like) and information about a curative treatment, such as an operation, radiotherapy, and massage. In addition, the intervention information includes various kinds of information about intervention for the patient. As one example, the database 20 stores an event of change from a cast to a bandage with recovery of the patient as the intervention information, associating with the information of time and date of the change and the patient ID. Moreover, as on example, the database 20 stores an event of application of a poultice to a portion for which the patient expressed pain as the intervention information, associating with the information of time and date of the application and the patient ID.

The medical information may be information recorded in a medical facility such as a clinic, a nursing home, and an examination facility, not limited to hospitals. Moreover, the medical information may be information recorded outside medical facilities, such as in a home of the patient. For example, the medical information may be information recorded in any place by a wearable device put on the patient.

The diagnosis supporting apparatus 10 is an apparatus that supports diagnosis by a user by performing various kinds of displays based on medical information acquired from the database 20. For example, the diagnosis supporting apparatus 10 includes, as illustrated in FIG. 1, an input interface 101, a display 102, a storage 103, and processing circuitry 104.

The input interface 101 receives various kinds of input operations from the user, and converts the received input operation into an electrical signal to output to the processing circuitry 104. For example, the input interface 101 is implemented by a mouse, a keyboard, a trackball, a switch, a button, a joystick, a touch pad that enables input operation by being touched on an operating surface, a touch screen in which a display screen and a touch pad are integrated, a non-contact input circuit using an optical sensor, a sound input circuit, or the like. The input interface 101 may be constituted of a tablet terminal that is capable of wireless communication with a main unit of the diagnosis supporting apparatus 10, or the like. Moreover, the input interface 101 is not limited to one having a physical operating part, such as a mouse and a keyboard. For example, a processing circuit of an electrical signal that receives an electrical signal corresponding to an input operation from an external input device provided separately from the diagnosis supporting apparatus 10, and that outputs this electrical signal to the processing circuitry 104 is also included in examples of the input interface 101.

The display 102 displays various kinds of information. For example, the display 102 displays a graphical user interface (GUI) to receive various instructions, various settings, and the like from the user through the input interface 101. Furthermore, the display 102 performs display based on a first change amount and a second change amount described later. For example, the display 102 is a liquid crystal display or a cathode ray tube (CRT) display. The display 102 may be of a desktop type, or may be constituted of a tablet terminal capable of wireless communication with the main unit of the diagnosis supporting apparatus 10.

The storage 103 is implemented by, for example, a random access memory (RAM), a semiconductor memory device such as a flash memory, a hard disk, an optical disk, or the like. For example, the storage circuit stores a program to cause a circuit included in the diagnosis supporting apparatus 10 to implement its function. The storage 103 may be implemented by a server group (cloud) connected to the diagnosis supporting apparatus 10 through the network NW.

The processing circuitry 104 controls overall operation of the diagnosis supporting apparatus 10 by performing an extracting function 104a, a calculating function 104b, a display control function 104c, and a control function 104d. The extracting function 104a is an example of an extracting unit. Moreover, the calculating function 104b is an example of a calculating unit. Furthermore, the display control function 104c is an example of a display control unit.

For example, the processing circuitry 104 acquires medical information from the database 20 through the network NW by reading and executing a program corresponding to the extracting function 104a from the storage 103, to extract a change point in the acquired medical information. Moreover, for example, the processing circuitry 104 calculates the first change amount that indicates a change of the patient information between before and after the change point, and a second change amount that indicates a change of the intervention information between before and after the change point by reading and executing a program corresponding to the calculating function 104b from the storage 103. Moreover, for example, the processing circuitry 104 performs display based on the first change amount and the second change amount on the display 102 by reading and executing a program corresponding to the display control function 104c from the storage 103. Furthermore, the processing circuitry 104 controls overall operation of the diagnosis supporting apparatus 10 based on an operation received from the user through the input interface 101 by reading and executing a program corresponding to the control function 104d from the storage 103. The respective functions of the processing circuitry 104 will be described in detail later.

In the diagnosis supporting apparatus 10 illustrated in FIG. 1, the respective functions are stored in the storage 103 in a form of computer-executable form. The processing circuitry 104 is a processor that implements the functions corresponding to the respective programs by reading and executing the respective programs from the storage 103. In other words, the processing circuitry 104 that has read the respective programs is to have the functions corresponding to the read programs.

Although it has been explained that the extracting function 104a, the calculating function 104b, the display control function 104c, and the control function 104d are implemented by a single unit of the processing circuitry 104 in FIG. 1, the functions may be implemented by configuring the processing circuitry 104 with plural independent processors combined, and by executing a program by each processor. Moreover, the respective functions of the processing circuitry 104 may be implemented by a single or plural processing circuits in a distributed manner or in an integrated manner.

It is noted that the diagnosis supporting apparatus 10 and the database 20 may be installed in any places as long as they can be connected to each other through the network NW. For example, the diagnosis supporting apparatus 10 may be installed in a different hospital from the database 20. That is, the network NW may be an in-hospital closed local network, or a network using the Internet.

The term "processor" used in the above explanation signifies, for example, a central processing unit (CPU), a graphics processing unit (GPU), or a circuit, such as an application specific integrated circuit (ASIC), a programmable logic device (for example, a simple programmable logic device (SPLD), a complex programmable logic device (CPLD)), and a field programmable gate array (FPGA). The processor implements a function by reading and executing a program stored in the storage 103.

In FIG. 1, it has been explained that a single unit of the storage 103 stores the programs corresponding to the respective functions. However, embodiments are not limited thereto. For example, it may be configured such that plural units of the storages 103 are arranged in a distributed manner, and the processing circuitry 104 reads a corresponding program from the individual storage 103. Moreover, instead of storing the programs in the storage 103, it may be configured to install the programs directly in a circuit of the processor. In this case, the processor implements a function by reading and executing the program installed in the circuit.

Moreover, the processing circuitry 104 may implement a function by using a processor of an external device connected through the network NW. For example, the processing circuitry 104 implements the respective functions illustrated in FIG. 1 by reading and executing programs corresponding to the respective functions from the storage 103, and by using a server group (cloud) connected to the diagnosis supporting apparatus 10 through the network NW as a calculation resource.

As above, the diagnosis supporting apparatus 10 and the database 20 have been explained. With such a configuration, the diagnosis supporting apparatus 10 in the diagnosis supporting system 1 facilitates understanding of medical information of a patient by processing performed by the processing circuitry 104. In the following, processing for a user to grasp medical information of a patient P1 will be explained as an example.

Figure 2:
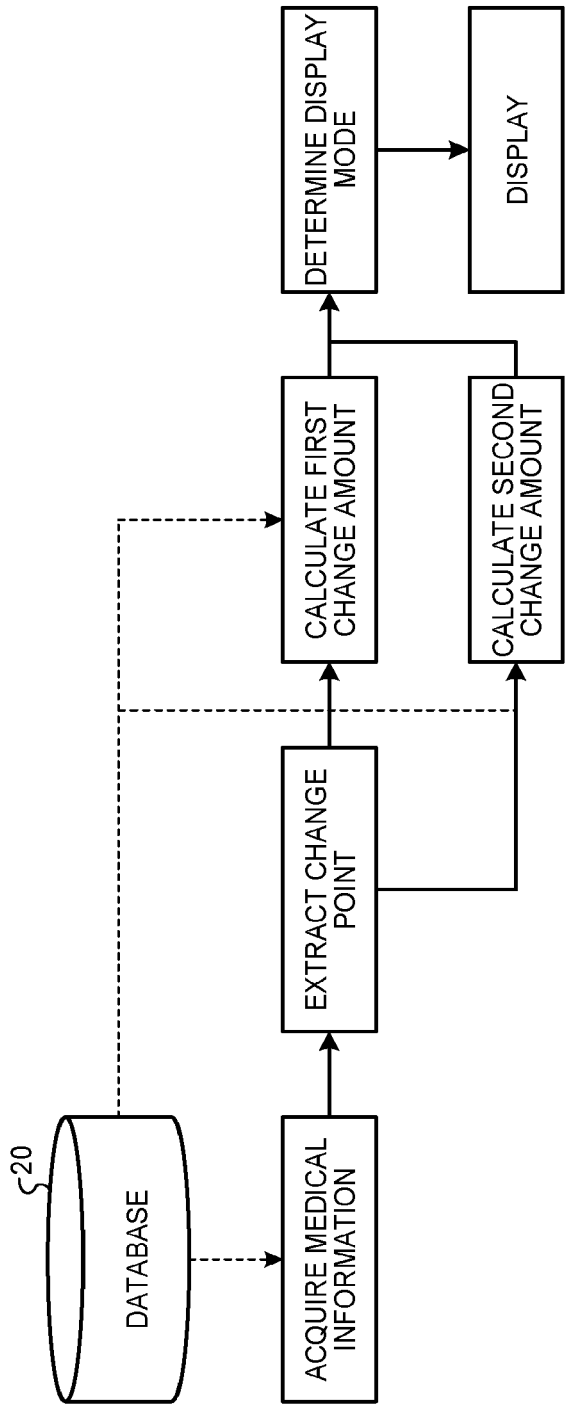
FIG. 2 is a diagram illustrating overview of processing performed by a diagnosis supporting apparatus according to the first embodiment.

First, overview of processing performed by the diagnosis supporting apparatus 10 will be explained, using FIG. 2. For example, the diagnosis supporting apparatus 10 first acquires medical information of the patient P1 from the database 20. For example, the diagnosis supporting apparatus 10 acquires the medical information including the patient information about the patient P1 and the intervention information based on the patient ID of the patient P1. FIG. 2 is a diagram illustrating overview of processing performed by the diagnosis supporting apparatus 10 according to the first embodiment.

Subsequently, the diagnosis supporting apparatus 10 extracts a change point in the medical information. Subsequently, the diagnosis supporting apparatus 10 calculates the first change amount that indicates a change in the patient information between before and after the change point, and the second change amount that indicates a change in the intervention information between before and after the change point. Subsequently, the diagnosis supporting apparatus 10 sets a display mode according to at least one of the first change amount and the second change amount. The diagnosis supporting apparatus 10 then performs display based on the first change amount and the second change amount in the set display mode.

Figure 3:
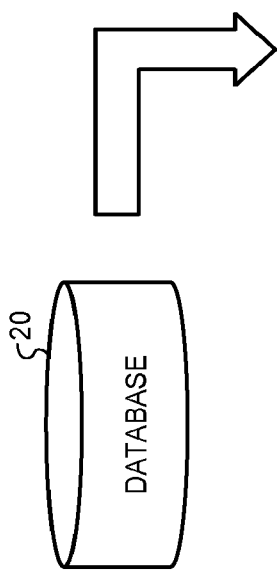
FIG. 3 is a diagram illustrating an example of medical information according to the first embodiment.

Next, the processing performed by the diagnosis supporting apparatus 10 will be explained in more detail. First, the medical information acquired from the database 20 will be explained, using FIG. 3. FIG. 3 is a diagram illustrating an example of the medical information according to the first embodiment. For example, the extracting function 104a acquires the intervention information and the patient information illustrated in FIG. 3 through the network NW. For example, the extracting function 104a acquires the intervention information and the patient information illustrated in FIG. 3 from the database 20, for example, triggered by reception of an instruction to perform diagnosis of the patient P1 from the user.

The intervention information illustrated in FIG. 3 is records of medication of a diuretic drug and a cardiotonic drug on respective days from "2019.5.17" to "2019.5.24". In other words, the intervention information illustrated in FIG. 3 is chronological information relating to medication of a diuretic drug and a cardiotonic drug.

Specifically, FIG. 3 indicates that a diuretic drug and a cardiotonic drug were not given on "2019.5.17". Moreover, FIG. 3 indicates that a diuretic drug was given in a dose of "10" and a cardiotonic drug was not given on "2019.5.18". Moreover, FIG. 3 indicates that a diuretic drug was given in a dose of "10" and a cardiotonic drug was given in a dose of "20" on "2019.5.19". Moreover, FIG. 3 indicates that a diuretic drug and a cardiotonic drug were not given on "2019.5.20". Moreover, FIG. 3 indicates that a diuretic drug was given in a dose of "10" and a cardiotonic drug was not given on "2019.5.21". Moreover, FIG. 3 indicates that a diuretic drug and a cardiotonic drug were not given on "2019.5.22", "2019.5.23", and "2019.5.24".

Furthermore, the patient information illustrated in FIG. 3 is a record of NT-proBNP and respiration rate per unit time on each day in a period from "2019.5.17" to "2019.5.24". In other words, the patient information illustrated in FIG. 3 is chronological information relating to NT-proBNP and respiration rate.

Specifically, FIG. 3 indicates that NT-proBNP was "192" and the respiration rate was "8" on "2019.5.17". Moreover, FIG. 3 indicates that NT-proBNP was "185" and the respiration rate was "12" on "2019.5.18". Moreover, FIG. 3 indicates that NT-proBNP was "200" and the respiration rate was "14" on "2019.5.19". Moreover, FIG. 3 indicates that NT-proBNP was "180" and the respiration rate was "13" on "2019.5.20". Moreover, FIG. 3 indicates that NT-proBNP was "92" and the respiration rate was "23" on "2019.5.21". Moreover, FIG. 3 indicates that NT-proBNP was "100" and the respiration rate was "21" on "2019.5.22". Moreover, FIG. 3 indicates that NT-proBNP was "89" and the respiration rate was "20" on "2019.5.23". Moreover, FIG. 3 indicates that NT-proBNP was "102" and the respiration rate was "19" on "2019.5.24".

Subsequently, the extracting function 104a extracts a change point in the medical information. For example, the extracting function 104a sets plural points of time for the chronological information illustrated in FIG. 3, compares features of the medical information between before and after each point of time, and extracts a point of time at which a degree of change is large as a change point.

Figure 4:
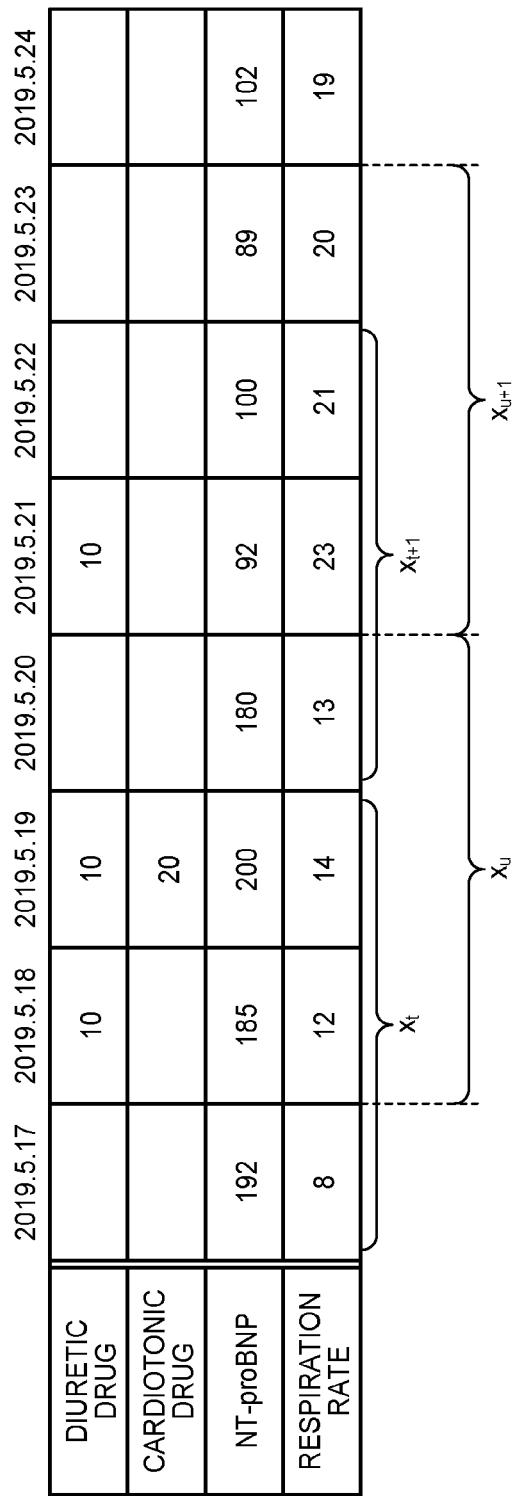
FIG. 4 is a diagram illustrating an example of extraction processing of a change point according to the first embodiment.

As one example, the extracting function 104a sets a period xt that is a three-day period of "2019.5.17 to 2019.5.19", and a period xt+1 that is a three-day period of "2019.5.20 to 2019 May 22" as illustrated in FIG. 4. FIG. 4 is a diagram illustrating an example of extraction processing of a change point according to the first embodiment.

Figure 5:
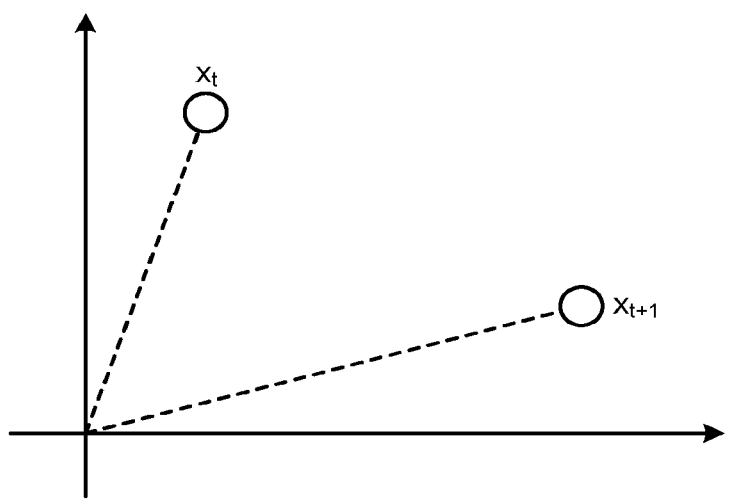
FIG. 5 is a diagram illustrating an example of the extraction processing of a change point according to the first embodiment.

Subsequently, the extracting function 104a evaluates a degree of change by comparing a feature vector indicating the medical information of the period xt and a feature vector indicating the medical information of the period xt+1, as illustrated in FIG. 5. For example, the extracting function 104a performs subtraction between the feature vector indicating the medical information of the period xt and the feature vector indicating the medical information of the period xt+1, and thereby evaluates a calculated magnitude of vector (norm) as a degree of change. FIG. 5 is a diagram illustrating an example of the extraction processing of a change point according to the first embodiment. For explanations' sake, a two dimensional vector is shown in FIG. 5, but each feature vector is to be a four-dimensional vector having dimensions corresponding to a diuretic drug, a cardiotonic drug, NT-proBNP, and a respiration rate.

Furthermore, the extracting function 104a evaluates a degree of change between a period xu that is a three-day period of "2019.5.18 to 2019.5.20" and a period xu+1 that is a three-day period of "2019.5.21 to 2019.5.23" as illustrated in FIG. 4. Similarly, the extracting function 104a evaluates a degree of change between a three-day period of "2019.5.19 to 2019.5.21" and a three-day period of "2019.5.22 to 2019.5.24". That is, the extracting function 104a evaluates a degree of change at each point of time while shifting a subject point of time. The extracting function 104a then extracts a point of time in which a degree of change is large, as a change point. For example, the extracting function 104a extracts a point of time at which a degree of change is larger than a threshold, as a change point.

In FIG. 4, a case in which a three-day period (the period xt, the period xt+1, the period xu, the period xu+1, and the like) is set at the time of evaluating a degree of change has been explained, but a length of the period to be set is not particularly limited. Moreover, the extracting function 104a may evaluate a degree of change while changing the length of the period to be set.

For example, the extracting function 104a evaluates a degree of change between the period xt that is the three-day period of "2019.5.17 to 2019.5.19" and the period xt+1 that is a three-day period of "2019.5.20 to 2019 May 22". Moreover, the extracting function 104a evaluates a degree of change between a two-day period of "2019.5.18 to 2019.5.19" and a two-day period of "2019.5.20 to 2019.5.21". Moreover, the extracting function 104a evaluates a degree of change between one-day period of "2019.5.19" and a one-day period of "2019.5.20". The extracting function 104a then determines whether to extract a point of time between "2019.5.19" and "2019.5.20" based on these three evaluations. For example, the extracting function 104a calculates a mean value of these three evaluations, and determines whether to extract the point of time between "2019.5.19" and "2019.5.20" as a change point according to whether the mean value exceeds a threshold. Moreover, the extracting function 104a determines similarly for respective other points of time in a period of "2019.5.17 to 2019.5.24" whether to extract as a change point. As described, by evaluating a degree of change while changing the length of the set period, the extracting function 104a can extract both a momentary change and a smooth change as a change point.

Alternatively, the extracting function 104a may perform extraction of a change point by using a subspace method. For example, the extracting function 104a acquires plural feature vectors from the period xt. Specifically, the extracting function 104a acquires plural feature vectors, such as a feature vector based on the three-day period of "2019.5.17 to 2019.5.19", a feature vector of the two-day period of "2019.5.17 to 2019.5.18", a feature vector of the two-day period of "2019.5.18 to 2019.5.19", a feature vector of the one-day period of "2019.5.17", a feature vector of the one-day period of "2019.5.18", a feature vector of the one-day period of "2019.5.19". Furthermore, the extracting function 104a calculates a subspace based on these plural feature vectors.

Similarly, the extracting function 104a acquires plural feature vectors from the period xt+1, and calculates a subspace based on the acquired plural feature vectors. The extracting function 104a compares the subspace based on the period xt and the subspace based on the period xt+1, and determines whether to extract a point of time between "2019.5.19" and "2019.5.20" as a change point. Moreover, the extracting function 104a determines similarly for respective other points of time in the period of "2019.5.17 to 2019.5.24" whether to extract as a change point.

Alternatively, the extracting function 104a may perform extraction of a change point by using a density ratio. For example, the extracting function 104a compares a distribution of the medical information in the period xt and a distribution of the medical information in the period xt+1. As one example, the extracting function 104a compares statistical values relating to deviation and shapes of distribution between the distribution of the medical information in the period xt and the distribution of the medical information in the period xt+1. The statistical value relating to deviation of distribution is, for example, a mean value of the respective distributions. Moreover, the statistical value relating to shapes of distribution is, for example, a variance of the respective distributions. The extracting function 104a determines whether to extract a point of time between "2019.5.19" and "2019.5.20" as a change point based on a result of comparison between the distributions. Moreover, the extracting function 104a determines similarly for respective other points of time in the period of "2019.5.17 to 2019.5.24" whether to extract as a change point.

The extracting function 104a may perform extraction of a change point by a technique of machine learning. For example, the extracting function 104a performs extraction of a change point by using a trained model M1 to which a function of extracting a change point in medical information is given. The trained model M1 is, for example, generated by the extracting function 104a in advance, and is stored in the storage 103.

For example, the extracting function 104a first collects training data to be used for generation of the trained model M1. For example, the extracting function 104a acquires a pair of medical information and a change point as training data. The medical information to be used as the training data may be medical information about the patient P1, or may be medical information about other patients.

Moreover, a change point to be used as the training data can be set by a user, such as a doctor. Alternatively, the extracting function 104a can set a change point to be used as the training data automatically. For example, the extracting function 104a can set a point of time when the user pays attention while referring to medical information, as a change point. As one example, the extracting function 104a can set a point of time corresponding to medical information that is displayed for a long time, or a point of time corresponding to medical information for which the user has instructed to provide details, as a change point.

Subsequently, the extracting function 104a performs machine learning based on the collected training data, to generate the trained model M1. The trained model M1 can be constituted of, for example, a neural network. The neural network has a structure in which adjacent layers aligned in layers are connected with each other, and is a network that propagates information from an input layer side to an output layer side. For example, the extracting function 104a generates the trained model M1 by performing deep learning for a multi-layer neural network, using the training data described above. The multi-layer neural network is constituted of, for example, an input layer, plural intermediate layers (hidden layers), and an output layer.

As one example, the extracting function 104a inputs medical information of one patient into the neural network as input data. In this case, the in the neural network, information is propagated in one direction from the input layer side toward the output layer side, while connecting only adjacent layers, and an estimation result of a change point in the input medical information is output from the output layer side. Note that the neural network in which information is propagated in one direction from the input layer side toward the output layer side is also called convolutional neural network (CNN). Although the CNN has been explained as an example, the extracting function 104a may user a different type of neural network from the CNN. For example, the extracting function 104a may configure the trained model M1 by using a neural network, such as a fully-connected neural network and a recurrent neural network (RNN).

The extracting function 104a generates the trained model M1 by adjusting parameters of the neural network such that the neural network can output a preferable result when input data is input. For example, the extracting function 104a repeats processing while adjusting parameters of the neural network until a difference between an estimation result of a change point output from the neural network and a change point input as training data of the output side becomes below a threshold. Thus, the extracting function 104a generates the trained model M1 to which a function of receiving an input of medical information and of extracting a change point in the input medical information is given. Moreover, the extracting function 104a causes the storage 103 to store the generated trained model M1.

The extracting function 104a inputs medical information about the patient P1 to the trained model M1. For example triggered by reception of an instruction to perform diagnosis of the patient P1 from the user, the extracting function 104a acquires the medical information from the database 20 and reads the trained model M1 from the storage 103, and inputs the medical information into the trained model M1. Furthermore, the trained model M1 outputs a change point in the input medical information. That is, the extracting function 104a can extract a change point in the medical information about the patient P1 by using the trained model M1.

Although it has been explained that input data for the trained model M1 is medical information, embodiments are not limited thereto. For example, the extracting function 104a may generate the trained model M1 by using a subspace or a density ratio calculated based on the medical information as input data instead of the medical information. In this case, the extracting function 104a calculates a subspace or a density ratio from the medical information about the patient P1, and inputs the calculated subspace of density ratio into the trained model M1, and thereby enabled to extract a change point in the medical information about the patient P1.

Moreover, although it has been explained that the trained model M1 is constituted of a neural network, the extracting function 104a may generate the trained model M1 by a machine learning method other than the neural network. Furthermore, although it has been explained that the extracting function 104a generates the trained model M1, the trained model M1 may be generated by a device other than the diagnosis supporting apparatus 10.

Subsequently, the extracting function 104a extracts the first period before the change point and the second period after the change point. For example, the extracting function 104a extracts periods of a preset length before and after the change point as the first period and the second period. In the following, a case in which the length of period is preset to "three days" will be explained as an example. For example, as illustrated in FIG. 6, when a change point V1 that is a point of time between "2019.5.19 to 2019.5.20" is extracted as a change point, the extracting function 104a extracts a period R11 that corresponds to three days preceding the change point V1 as the first period, and extracts a period R12 that corresponds to three days following the change point V2 as the second period. FIG. 6 is a diagram illustrating an example of extraction processing of the first period and the second period according to the first embodiment.

Alternatively, the extracting function 104a may extract periods between plural extracted change points as the first period and the second period. For example, when the change point V1 that is a point of time between "2019.5.19 to 2019.5.20", the change point V2 that is a point of time between "May 16, 2019 to 2019.5.17", and a change point V3 that is a point of time V1 between "2019.5.23 to 2019.5.24" are extracted as the change point, the extracting function 104a extracts a period R21 and a period R22 as illustrated in FIG. 7 for the change point V1. That is, the extracting function 104a extracts the period R21 between the change point V1 and the change point V2 as the first period preceding the change point V1. Moreover, the extracting function 104a extracts the period R22 between the change point V1 and the change point V3 as the second period following the change point V1. FIG. 7 is a diagram illustrating an example of the extraction processing of the first period and the second period according to the first embodiment. Setting an upper limit value for a length of the period, the extracting function 104a may extracts the first period and the second period based on the upper limit value when a period between change points is long.

Subsequently, the calculating function 104b calculates a first change amount that indicates a change of the patient information between before and after the change point, and a second change amount that indicates a change of the intervention information between before and after the change point. For example, the calculating function 104b calculates the first change amount based on the patient information in the first period and the patient information in the second period, and calculates the second change amount based on the intervention information in the first period and the intervention information in the second period. In the following, a case in which the period R11 and the period R12 are extracted as periods preceding and following the change point V1 by the extracting function 104a will be explained.

Figure 8:
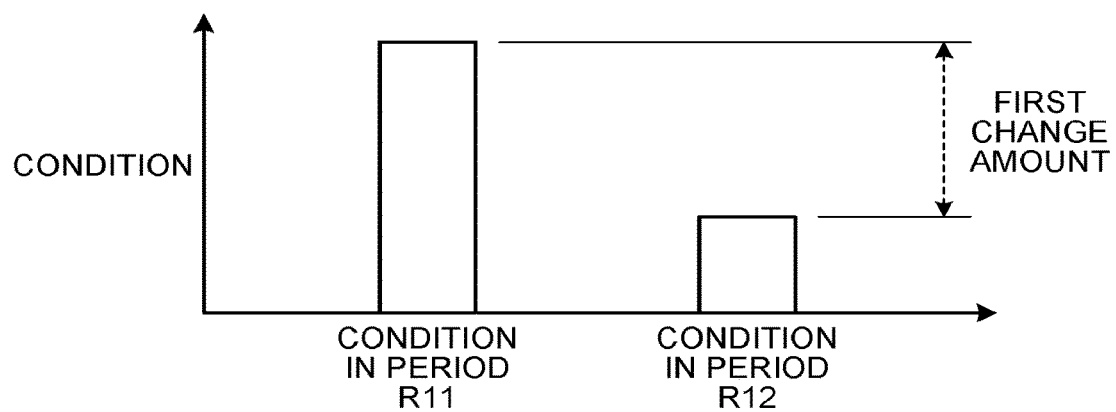
FIG. 8 is a diagram illustrating an example of calculation processing of a first change amount according to the first embodiment.

First, calculation of the first change amount will be explained by using FIG. 8. FIG. 8 is a diagram illustrating an example of calculation processing of the first change amount according to the first embodiment. As illustrated in FIG. 8, the calculating function 104b respectively calculates a condition in the period R11 and a condition in the period R12, and calculates a difference in condition as the first change amount.

Specifically, the calculating function 104b calculates a condition in the period R11 based on the patient information in the period R11. That is, the calculating function 104b calculates the condition in the period R11 based on NT-proBNP and the respiration rate of the patient P1 in the period of "2019.5.17 to 2019.5.19". The calculating function 104b may calculate a numerical value indicating a condition as the condition in the period R11, or may perform sorting to plural ranks indicating conditions. Numerical values indicating a condition and a rank setting method are not particularly limited, and it may be, for example, ones set by the user, ones set in each hospital, or ones set based on guidelines generally used, or the like.

For example, the calculating function 104b calculates the condition in the period R11 according to a predetermined table in which respective values of NT-proBNP and a respiration rate and a condition are associated with each other. Moreover, for example, the calculating function 104b calculates the condition in the period R11 according to a predetermined table in which a combination of NT-proBNP and a respiration rate and a condition are associated with each other.

Moreover, for example, the calculating function 104b may be configured to calculate the condition in the period R11 based on a predetermined mathematical expression. As one example, the calculating function 104b calculates a variance of NT-proBNP and the respiration rate in the period R11, as the condition in the period R11.

Alternatively, the calculating function 104b may be configured to calculate the condition in the period R11 by a machine learning method. For example, the calculating function 104b calculates the condition in the period R11 by using a trained model M2 to which a function of receiving an input of patient information and of outputting a condition is given. The trained model M2 is generated by the calculating function 104b in advance, and is stored in the storage 103.

For example, the calculating function 104b first collects training data to be used for generation of the trained model M2. For example, the calculating function 104b acquires a pair of patient information and a condition as the training data. The patient information used as the training data may be the patient information about the patient P1, or may be patient information about another patient. Moreover, the condition input as the training data can be set by the user, such as a doctor. For example, the user can set the condition based on a result of interview performed at the time when the patient information in the pair is acquired, or the like.

Subsequently, the calculating function 104b performs machine learning based on the collected training data, to generate the trained model M2. The trained model M2 can be constituted by, for example, a neural network. For example, the calculating function 104b can generate the trained model M2 by performing deep learning for a multi-layered neural network by using the training data described above. Furthermore, the calculating function 104b causes the storage 103 to store the generated trained model M2.

The calculating function 104b then inputs the patient information about the patient P1 into the trained model M2 read from the storage 103. Moreover, the trained model M2 outputs the condition in the period R11 based on the input patient information. That is, the calculating function 104b can calculate the condition in the period R11 by using the trained model M2.

Although it has been explained that the trained model M2 is constituted of a neural network, the calculating function 104b may generate the trained model M2 by a machine learning method other than the neural network. Furthermore, although it has been explained that the calculating function 104b generates the trained model M2, the trained model M2 may be generated by a device other than the diagnosis supporting apparatus 10.

As described above, the calculating function 104b calculates the condition in the period R11 based on the patient information in the period R11. Similarly, the calculating function 104b calculates the condition in the period R12 based on the patient information in the period R12. The calculating function 104b calculates the first change amount based on the condition in the period R11 and the condition in the period R12. For example, when a numerical value is calculated as the condition, the calculating function 104b calculates a difference in numerical value between the condition in the period R11 and the condition in the period R12 as the first change amount. Moreover, for example, when a rank is calculated as the condition, the calculating function 104b calculates a difference in rank number between the condition in the period R11 and the condition in the period R12 as the first change amount.

The calculating function 104b may perform normalization about the first change amount. For example, the calculating function 104b may normalize the first change amount calculated within an arbitrary numerical range, or the first change amount calculated as a rank to be a numerical value of "0 to 1". Alternatively, the calculating function 104b may normalize the first change amount such that a sum with the second change amount described later is to be "1". In the following, the normalized first change mount is also denoted as condition change degree.

Figure 9:
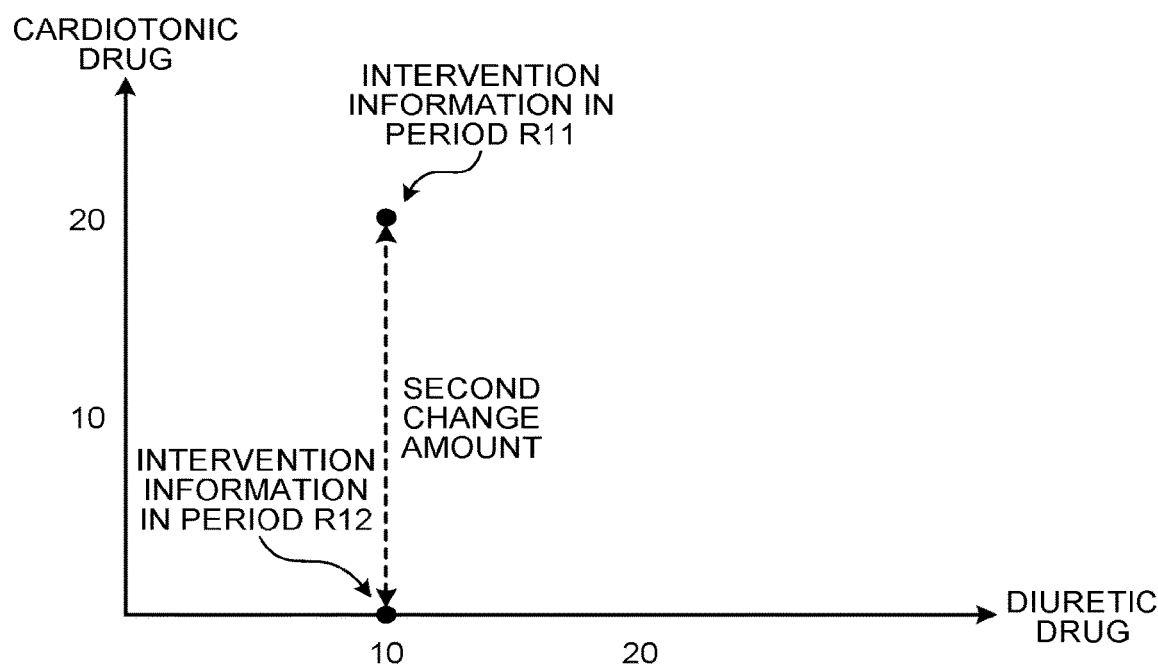
FIG. 9 is a diagram illustrating an example of calculation processing of a second change amount according to the first embodiment.

Next, calculation of the second change amount will be explained by using FIG. 9. FIG. 9 is a diagram illustrating an example of calculation processing of the second change amount according to the first embodiment. As illustrated in FIG. 9, the calculating function 104b converts the intervention information in the period R11 and the intervention information in the period R12 into vectors, and calculates the second change amount by comparing the vectors.

For example, the calculating function 104b can convert the intervention information in the period R11 and the period R12 into vectors by using a representative value (for example, a maximum value, or a value near a change point, or the like) in each period. Specifically, the intervention information in the period R11 can be expressed as a vector, (diuretic drug, cardiotonic drug)=(10, 20). Moreover, the intervention information in the period R12 can be expressed by a vector, (diuretic drug, cardiotonic drug)=(10, 0). The calculating function 104b calculates the second change amount by comparing these two vectors. For example, the calculating function 104b calculates the second change amount by performing subtraction between these two vectors as illustrated in FIG. 9.

The calculating function 104b may convert the intervention information in the period R11 and the period R12 by using other statistical values (for example, a mean value, or the like) in each period. Moreover, when whether an operation or the like has been conducted is used as the intervention information, the calculating function 104b can calculates the second change amount similarly to the case illustrated in FIG. 9, by converting into numerical values as "yes" into "1", and "no" into "0". Moreover, for explanations' sake, two-dimensional vectors have been explained in FIG. 9, but the dimensionality of vectors is not particularly limited.

Moreover, the calculating function 104b may perform normalization about the second change amount. For example, the calculating function 104b may normalize the second change amount calculated within an arbitrary numerical range to be a numerical value of "0 to 1". Alternatively, the calculating function 104b may normalize the second change amount such that a sum of the first change amount and the second change amount is to be "1". In the following, the normalized second change mount is also denoted as intervention change degree.

Figure 10A:
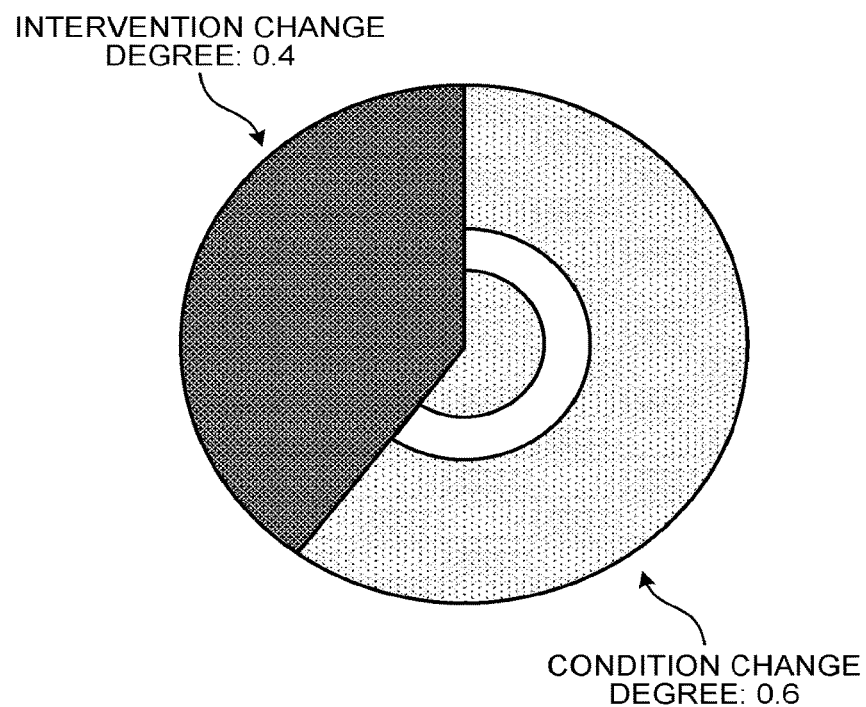
FIG. 10A is a diagram illustrating an example of display-mode setting processing according to the first embodiment.
Figure 10B:
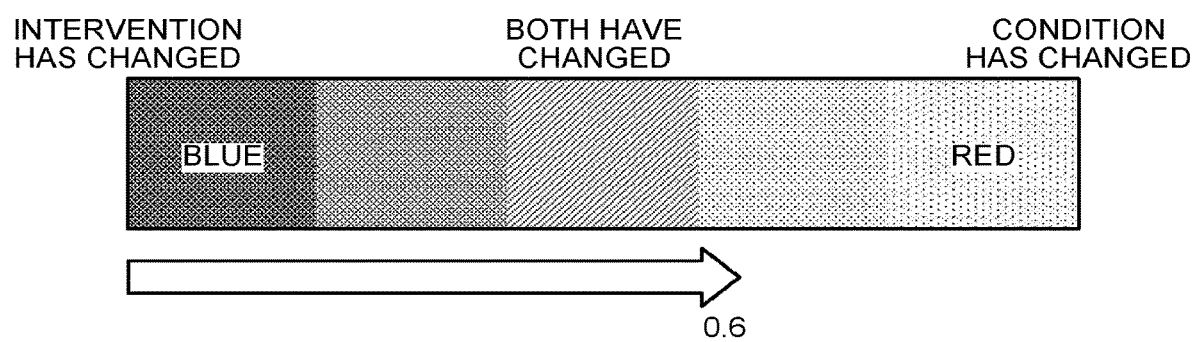
FIG. 10B is a diagram illustrating an example of the display mode setting processing according to the first embodiment.

Next, the display control function 104c sets a display mode according to at least one of the first change amount and the second change amount. For example, the display control function 104c sets the display mode according to a ratio between the first change amount and the second change amount. In the following, setting processing of the display mode will be explained by using FIG. 10A and FIG. 10B. FIG. 10A and FIG. 10B are diagrams illustrating an example of setting processing of the display mode according to the first embodiment.

First, the calculating function 104b normalizes the first change amount and the second change amount such that a sum of the first change amount and the second change amount becomes "1" as illustrated in FIG. 10A. FIG. 10A illustrates a case in which the condition change degree, which is the normalized first change amount, is "0.6" and the intervention change degree, which is the normalized second change amount, is "0.4".

Subsequently, the display control function 104c sets a mixed color in which two colors are mixed in a ratio according to the ratio between the first change amount and the second change amount. Specifically, the display control function 104c sets the mixed color in which red and blue are mixed to be "red:blue=6:4" according to the ratio of the condition change degree "0.6" and the intervention change degree "0.4". That is, the display control function 104c sets the mixed color to be more red when the change in condition is large with respect to the change in intervention, and sets the mixed color to be more blue when the change in intervention is large with respect to the change in condition, and sets the mixed color to be an intermediate color (purple) when the condition and the intervention are both changed about the same degree.

The display control function 104c then performs display based on the first change amount and the second change amount by using the set mixed color. For example, the display control function 104c shows a change point by using the set mixed color, while performing chronological display based on at least one of the patient information and the intervention information.

For example, the display control function 104c shows a change point with a bar, while chronologically displaying NT-proBNP and a respiration rate in a graph as illustrated in FIG. 11A. The bar indicating a change point in FIG. 11A is displayed in the mixed color set according to the ratio between the first change amount and the second change amount. More specifically, FIG. 11A illustrates a case in which a change point is shown in the mixed color set to be more red when the change in condition is large with respect to the change in intervention. FIG. 11A is a diagram illustrating a display example according to the first embodiment.

The user that refers to the display in FIG. 11A can understand that there is a change point between "2019.5.20" and "2019.5.21", and that the change in condition is large with respect to the change in intervention at a glance. That is, the user can understand easily that the condition of the patient P1 was changed relatively greatly by the intervention performed between "2019.5.20" and "2019.5.21". In other words, the user can understand about the intervention performed between "2019.5.20" and "2019.5.21" easily that it caused a great influence on the condition of the patient P1.

Figure 11B:
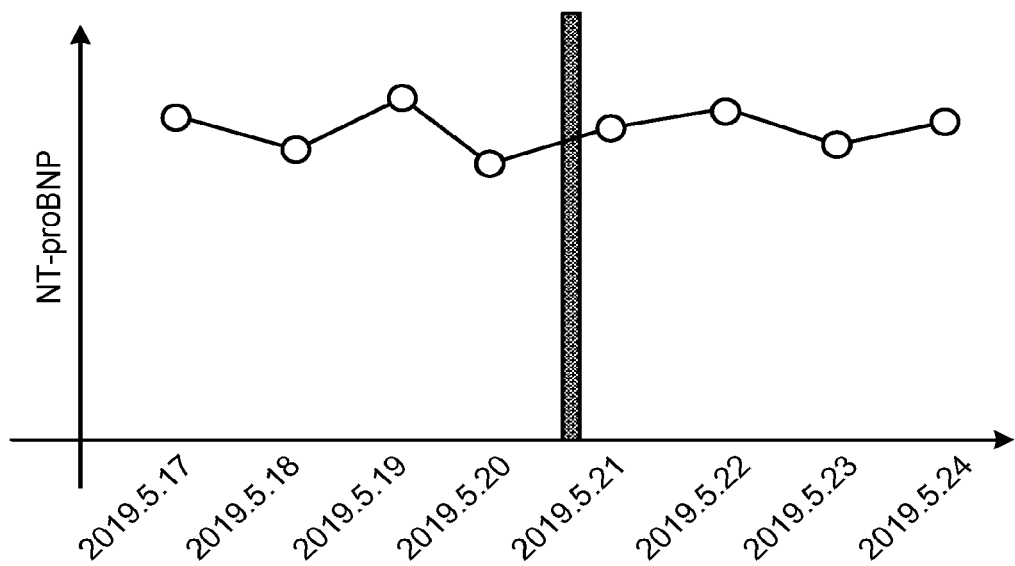
FIG. 11B is a diagram illustrating a display example according to the first embodiment.
Figure 11B:
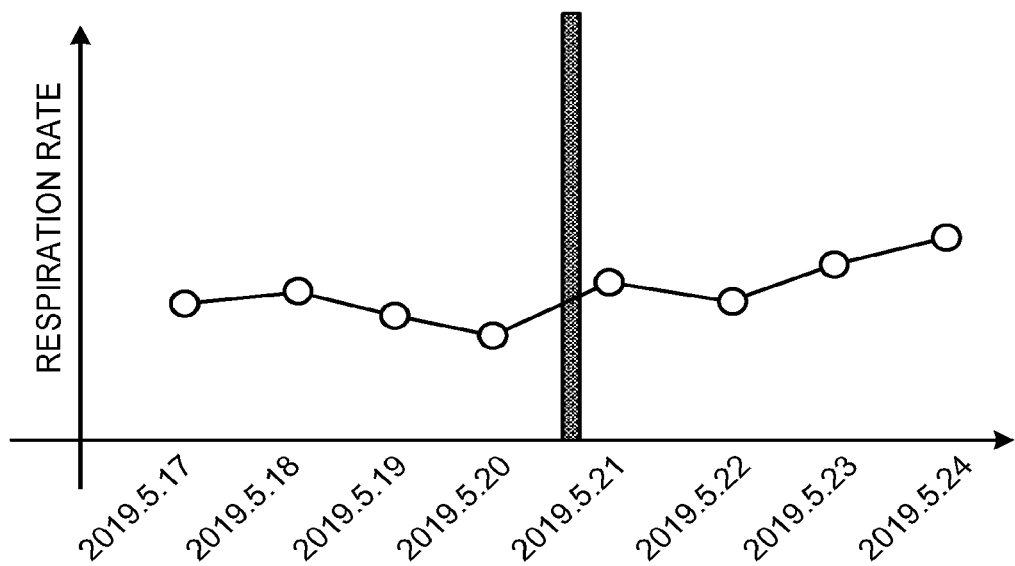

Moreover, for example, the display control function 104c shows a change point with a bar, while chronologically displaying NT-proBNP and a respiration rate in a graph as illustrated in FIG. 11B. The bar indicating a change point in FIG. 11B is displayed in the mixed color set according to the ratio between the first change amount and the second change amount. More specifically, FIG. 11B illustrates a case in which a change point is shown in the mixed color set to be more blue when the change in condition is small with respect to the change in intervention. FIG. 11B is a diagram illustrating a display example according to the first embodiment.

The user that refers to the display in FIG. 11B can understand that there is a change point between "2019.5.20" and "2019.5.21", and that the change in condition is small with respect to the change in intervention at a glance. That is, the user can understand easily that the condition of the patient P1 stayed relatively unchanged after the intervention performed between "2019.5.20" and "2019.5.21". In other words, the user can understand about the intervention performed between "2019.5.20" and "2019.5.21" easily that it caused a small influence on the condition of the patient P1.

Figure 11C:
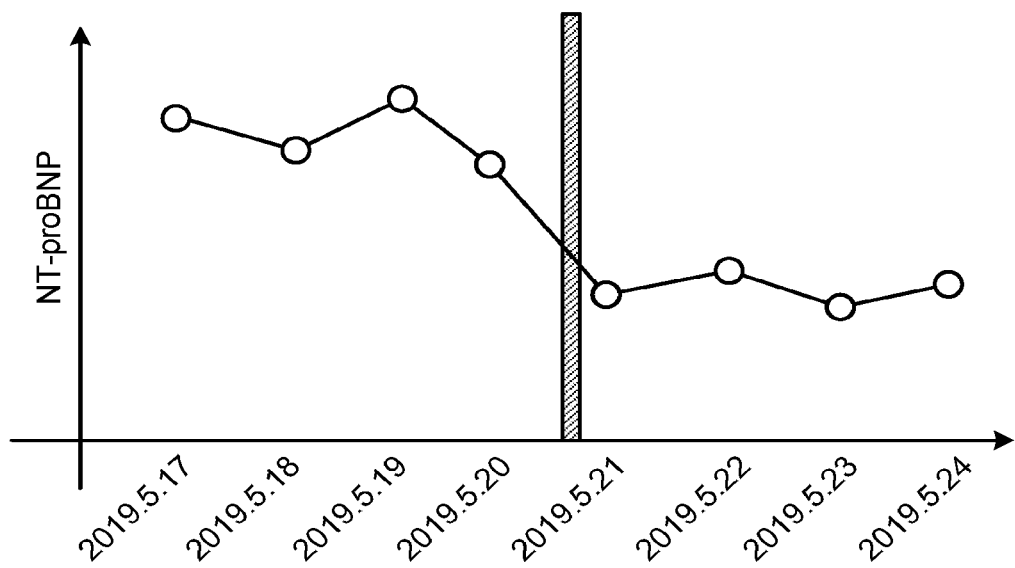
FIG. 11C is a diagram illustrating a display example according to the first embodiment.
Figure 11C:
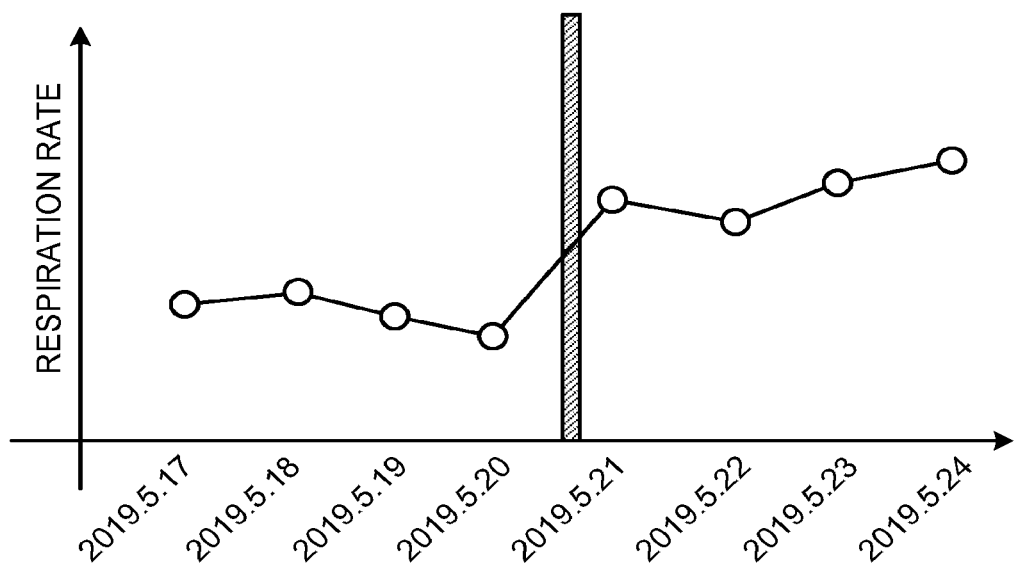

Moreover, for example, the display control function 104c shows a change point with a bar, while chronologically displaying NT-proBNP and a respiration rate in a graph as illustrated in FIG. 11C. The bar indicating a change point in FIG. 11C is displayed in the mixed color set according to the ratio between the first change amount and the second change amount. More specifically, FIG. 11C illustrates a case in which a change point is shown in the mixed color set to be the intermediate color (purple) when the condition and the intervention have changed about the same degree. FIG. 11C is a diagram illustrating a display example according to the first embodiment.

The user that refers to the display in FIG. 11C can understand that there is a change point between "2019.5.20" and "2019.5.21", and that the change in condition with respect to the change in intervention is an average degree at a glance. That is, the user can understand easily that the condition of the patient P1 has changed to an extent that is generally expected to the degree of intervention, by the intervention performed between "2019.5.20" and "2019.5.21".

In FIG. 11A, FIG. 11B, and FIG. 11C, a case in which NT-proBNP and a respiration rate are shown in a graph as an example of chronological display. However, embodiments are not limited thereto. For example, the display control function 104c may display patient information other than NT-proBNP and a respiration rate in a graph, or may display the intervention information in a graph.

Moreover, the display control function 104c may perform chronological display by using a table as illustrated in FIG. 11D. In this case, the display control function 104c can show a change point by displaying a bar on the table. FIG. 11D illustrates a case in which a change point is shown in the mixed color set to be in the intermediate color (purple) when the condition and the intervention both changed about the same degree. Moreover, FIG. 11D is a diagram illustrating a display example according to the first embodiment.

Moreover, the display control function 104c may display additional information other than the bars shown in FIG. 11A, FIG. 11B, FIG. 11C, and FIG. 11D. For example, the display control function 104c may display the first change amount, the second change amount, patient information other than NT-proBNP and the respiration rate, the intervention information, and the like, adding text annotations near the bar. As one example, the display control function 104c may display the first change amount, the second change amount, the patient information, the intervention information, and the like sequentially, while changing a display content each time the user makes a click operation to the bar. Furthermore, as one example, the display control function 104c may display more detailed information additionally, each time the user makes a click operation to the bar.

Figure 12:
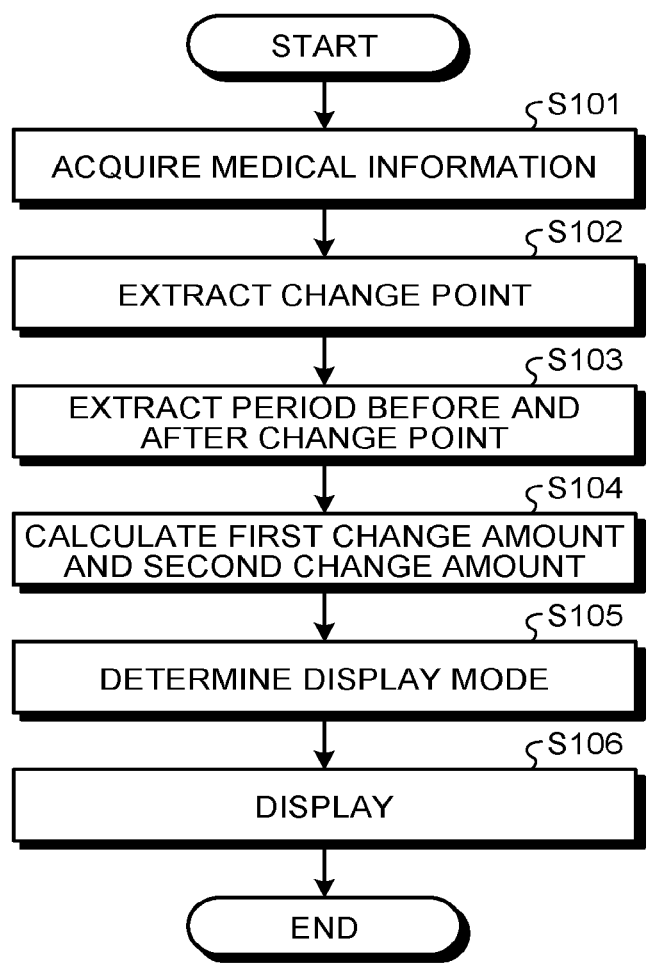
FIG. 12 is a flowchart for explaining a series of flow of processing performed by diagnosis supporting system according to the first embodiment.

Next, an example of procedure of processing performed by the diagnosis supporting system 1 will be explained by using FIG. 12. FIG. 12 is a flowchart for explaining a series of flow of the processing performed by diagnosis supporting system 1 according to the first embodiment. Step S101, step S102, and step S103 are steps corresponding to the extracting function 104a. Moreover, step S104 is a step corresponding to the calculating function 104b. Furthermore, step S105 and step S106 are steps corresponding to the display control function 104c.

First, the processing circuitry 104 acquires medical information that includes the patient information about the patient P1 and the intervention information relating to an intervention for the patient P1 (step S101). Subsequently, the processing circuitry 104 extracts a change point in the medical information (step S102). Subsequently, the processing circuitry 104 extracts the first period preceding the change point and the second period following the change point (step S103).

Subsequently, the processing circuitry 104 calculates the first change amount based on the patient information in the first period and the patient information in the second period, and calculates the second change amount based on the intervention information in the first period and the intervention information in the second period (step S104). Subsequently, the processing circuitry 104 sets the display mode according to at least one of the first change amount and the second change amount (step S105). Subsequently, the processing circuitry 104 performs display based on the first change amount and the second change amount in the set display mode (step S106), and ends the processing.

As described above, according to the first embodiment, the database 20 stores the medical information that includes the patient information about a condition of the patient P1, and the intervention information relating to an intervention for the patient P1. Moreover, the extracting function 104a extracts a change point in the medical information. Moreover, the calculating function 104b calculates the first change amount indicating a change in the patient information between before and after the change point, and the second change amount indicating a change in the intervention information between before and after the change point. Moreover, the display control function 104c performs display based on the first change amount and the second change amount in a display mode set according to at least one of the first change amount and the second change amount. Therefore, the diagnosis supporting system 1 according to the first embodiment can facilitate understanding of the medical information about the patient P1.

For example, the user that refers to the displays in FIG. 11A to FIG. 11D can be aware of the change point in the medical information based on a position of the bar, and grasp the first change amount and the second change amount at the respective change points by the color of the bar. That is, according to the diagnosis supporting system 1 according to the first embodiment, the user can grasp overviews of medical information easily even when a large number of change points are extracted. Furthermore, by grasping the overview in advance, the user can expand detailed medical information effectively according to a purpose, and can grasp it sequentially.

As another method for a user to grasp medical information, it can be considered that the user accesses the database 20 by himself/herself, to refer to medical information. However, because a large amount of medical information can be stored in the database 20, the user is to refer to the medical information while choosing it, and this process is to be a burden on the user.

Moreover, as another method for a user to grasp medical information, reference to a summary can be considered. The summary is a file that is generated based on a medical chart generated in past, and is generated, for example, at the time of transfer to another hospital, or at the time of discharge from a hospital. That is, the summary is a summary of medical information about a patient until transfer to another hospital or discharge from the hospital. However, because a large amount of information can be described in the summary depending on a patient, it is not easy for the user to grasp the entire medical information described therein. Moreover, for example, when it is desired to grasp a detailed change in the medical information, the information described in the summary can be insufficient.

Furthermore, as another method for a user to grasp medical information, it can be considered to extract a part of the medical information stored in the database 20 automatically, to present it to the user. For example, by automatically extracting a change point in medical information, and by extracting only medical information relating to the change point, it is thought that reduction of an amount of medical information to be presented to the user is possible. However, a large number of change points can be identified depending on a patient. In this case, a large amount of medical information is extracted, and a burden on the user that grasp the medical information can increase.

On the other hand, the diagnosis supporting system 1 calculates the first change amount and the second change amount based on an extracted change point, and display based on the first change amount and the second change amount is performed in a display mode set according to at least one of the first change amount and the second change amount. That is, the diagnosis supporting system 1 does not only extract medical information according to a change point, but also displays it in an abstracted manner. Thus, the user can grasp a change in the medical information intuitively and easily.

The first embodiment has been explained hereinabove, but other than the embodiment described above, it can be implemented in various different modes.

For example, in FIGS. 11A to 11D, the case in which the display mode is set according to the ratio between the first change amount and the second change amount has been explained, but embodiments are not limited thereto. For example, the display control function 104c may set a display mode according to respective magnitude of the first change amount and the second change amount, in addition to a ratio between the first change amount and the second change amount.

For example, the calculating function 104b respectively normalizes the first change amount and the second change amount to fall within a numerical range of "0 to 1". That is, the calculating function 104b calculates the condition change degree with the numerical range of "0 to 1", and calculates the intervention change degree with a numerical range of "0 to 1". Next, the display control function 104c sets the display mode according to the ratio between the condition change degree and the intervention change degree, and the respective magnitudes of the condition change degree and the intervention change degree.

As one example, the display control function 104c mixes two colors in a ratio according to the ratio between the condition change degree and the intervention change degree, and sets a mixed color for which a chroma is set according to the amount of a sum of the condition change degree and the intervention change degree. For example, the display control function 104c sets the mixed color such that the chroma increases as the sum of the condition change amount and the intervention change amount increases.

The display control function 104c then performs chronological display based on at least one of the patient information and the intervention information, and shows a change point with a bar colored with the set mixed color, similarly to the cases illustrated in FIG. 11A to 11D. In this case, the user grasp a change point in the medical information based on a position of the bar, and can grasp the ratio between the first change amount and the second change amount and the respective magnitudes based on the color of the bar. For example, in a case in which red and blue are used similarly to FIG. 10B, the user can grasp, when the bar is in a bright red, that a change in condition is larger with respect to a change in intervention, and that the change in condition is a drastic change. Moreover, for example, when the bar is in dark red, the user can grasp that although the change in condition is large with respect to the change in intervention, the change in condition is a small change.

As another example, the display control function 104c sets a mixed color in which two colors are mixed in a ratio according to a ratio between the condition change degree and the intervention change degree, and sets a mode of the bar according to a magnitude of a sum of the condition change degree and the intervention change degree. For example, the display control function 104c sets the thickness of the bar such that the thickness increases as the sum of the condition change degree and the intervention change degree increases. Moreover, for example, the display control function 104c displays the bar in a dotted line, and sets intervals such that the intervals between dots become narrower as the condition change degree and the intervention change degree increases. Furthermore, for example, the display control function 104c sets the transparency of the bar such that the transparency decreases as the sum of the condition change degree and the intervention change degree increases.

The display control function 104c then shows, similarly to the cases illustrated in FIGS. 11A to 11D, a change point with the bar in the set mixed color and mode, while performing chronological display based on at least one of the patient information and the intervention information. In this case, the user can be aware of the change point in the medical information based on a position of the bar, grasp the ratio between the first change amount and the second change amount based on the color of the bar, and further grasp the magnitude of the first change amount and the second change amount based on the mode of the bar.

Moreover, although it has been explained that a change point is indicated by using a bar in FIGS. 11A to 11D, embodiments are not limited thereto. For example, the display control function 104c may show a change point by using a shape other than a bar, or may indicate the change point with text. As one example, the display control function 104c may indicate a change point by using a shape, such as an arrow and a triangle, colored with the mixed color according to the ratio between the first change amount and the second change amount. As another example, the display control function 104c may indicate a change point by using text using the mixed color according to the ratio between the first change amount and the second change amount as its font color.

Moreover, it has been explained hereinabove that the mixed color made by mixing two colors in a ratio according to a ratio between the first change amount and the second change amount, but embodiments are not limited thereto. That is, setting a color as a display mode is only one example, and the display control function 104c may set a display mode other than the color. For example, the display control function 104c may be configured to set order of displaying the first change amount and the second change amount as a display mode, and to display the first change amount and the second change amount in the set order.

For example, the calculating function 104b respectively normalizes the first change amount and the second change amount to fall within a numerical range of "0 to 1". that is, the calculating function 104b calculates the condition change degree in the numerical range of "0 to 1", and calculates the intervention change degree in the numerical range of "0 to 1". Subsequently, the display control function 104c sets the order of displaying the condition change degree and the intervention change degree, according to the condition change degree and the intervention change degree.

As one example, the display control function 104c sets the order of displaying the condition change degree and the intervention change degree giving a higher priority as the intervention change degree increases and the condition change degree decreases. That is, the display control function 104c determines the order such that the intervention change degree is in descending order and the condition change degree is in ascending order. FIG. 13 is a diagram illustrating a display example according to a second embodiment.

Specifically, in the case illustrated in FIG. 13, the priority of the condition change degree "0.9" indicating a change in the patient information between before and after a change point "2019.5.20 23.34.24" and the intervention change degree "0.1" indicating a change in the intervention information is "1". Moreover, the priority of the condition change degree "0.8" indicating a change in the patient information between before and after a change point "2019.5.19 08.54.23" and the intervention change degree "0.2" indicating a change in the intervention information is "2". Moreover, the priority of the condition change degree "0.2" indicating a change in the patient information between before and after a change point "2019.5.23 12.12.11" and the intervention change degree "0.2" indicating a change in the intervention information is "3". Moreover, the priority of the condition change degree "0.1" indicating a change in the patient information between before and after a change point "2019.5.20 11.12.11" and the intervention change degree "0.6" indicating a change in the intervention information is "4". Moreover, the priority of the condition change degree "0.1" indicating a change in the patient information between before and after a change point "2019.5.21 14.43.21" and the intervention change degree "0.7" indicating a change in the intervention information is "5". Moreover, the priority of the condition change degree "0.2" indicating a change in the patient information between before and after a change point "2019.5.17 11.32.43" and the intervention change degree "0.9" indicating a change in the intervention information is "6".

In the case illustrated in FIG. 13, the display control function 104c can perform display such that the priority is higher as the change in condition becomes smaller relative to the change in the intervention. Thus, the user can find a treatment that did not produce any effect, or a treatment, the effect of which is small easily. The display control function 104c may be configured to further display the patient information and the intervention information before and after the change point as illustrated in FIG. 13.

The display control function 104c may be configured to set the order of displaying the condition change degree and the intervention change degree such that the priority is higher as the intervention change degree decreases and the condition change degree increases. In this case, the display control function 104c can perform display giving a higher priority as the change in condition becomes larger relative to the change in intervention. Thus, the user can find, for example, an effective treatment easily.

Alternatively, the display control function 104c may be configured to set the order of displaying the condition change degree and the intervention change degree giving a higher priority as the condition change degree increases. That is, the display control function 104c may set the order of displaying the condition change degree and the intervention change degree based only on the first change amount. Alternatively, the display control function 104c may be configured to set the order of displaying the condition change degree and the intervention change degree giving a higher priority as the intervention change degree increases. That is, the display control function 104c may set the order of displaying the condition change degree and the intervention change degree based only on the second change amount.

Furthermore, in the above embodiment, the case in which the first period preceding a change point and the second period following the change point are extracted, the first change amount is calculated based on the patient information in the first period and the patient information in the second period, and the second change amount is calculated based on the intervention information in the first period and the intervention information in the second period has been explained. However, embodiments are not limited thereto, and the extraction of the first period and the second period by the extracting function 104a may be omitted. In this case, the calculating function 104b can calculate the first change amount based on the patient information before the change point and the patient information after the change point. Moreover, the calculating function 104b can calculate the second change amount based on the intervention information before the change point and the intervention information after the change point.

Moreover, after the first change amount and the second change amount are calculated for the patient P1, the extracting function 104a may extract another patient P2, the first change amount and the second change amount of which resemble. For example, the extracting function 104a extracts the patient P2 having a distribution of change points on a time axis and values of the first change amount and the second change amount calculated for respective change points similar to those of the patient P1, and acquires medical information about the patient P2 from the database 20.

For example, when the patient P1 is in hospital and the patient P2 has been discharged from a hospital, the extracting function 104a acquires medical information in an entire period until discharge from the hospital out of the medical information about the patient P2. Moreover, the display control function 104c displays the medical information about the patient P2 on the display 102. Thus, the user can predict a future condition change of the patient P1 by referring to the patient information about conditions of the patient P2, or can make an intervention plan for the patient P1 by referring to the intervention information about a intervention for the patient P2.

Moreover, in the embodiment described above, it has been explained that the medical information including the patient information and the intervention information is stored in the database 20. However, embodiments are not limited thereto. For example, the medical information may be stored in the storage 103 of the diagnosis supporting apparatus 10.

The respective components of the respective devices according to the embodiments described above are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, the diagnosis supporting method described in the above embodiments can be implemented by executing a program that has been prepared in advance by a computer such as a personal computer and a workstation. This program can be distributed through a network such as the Internet. Furthermore, this program can be recorded on a non-transient recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments explained above, understanding of medical information about a patient can be facilitated.

According to the diagnosis supporting system of the embodiments, understanding of medical information about a patient can be facilitated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A diagnosis supporting system, comprising:
a memory that stores medical information including patient information relating to a medical condition of a patient, and intervention information relating to a medical intervention for the patient; and
processing circuitry configured to
extract a change point in the stored medical information,
calculate a first change amount indicating a change in the patient information between before and after the change point, and a second change amount indicating a change in the intervention information between before and after the change point, and
perform display of at least one of the patient information and the intervention information based on the calculated first change amount and the calculated second change amount in a display mode set by the processing circuitry according to a ratio between the calculated first change amount and the calculated second change amount, so as to visually indicate a relationship between the first and second change amounts, wherein the processing circuitry is further configured to display an icon representing the extracted change point, and display one of the first change amount, the second change amount, the patient information, and the intervention information adjacent to the icon, in response to selection of the icon by a user.

2. The diagnosis supporting system according to claim 1, wherein the processing circuitry is further configured to
extract a first period preceding the change point and a second period following the change point,
calculate the first change amount based on the patient information in the first period and the patient information in the second period, and
calculate the second change amount based on the intervention information in the first period and the intervention information in the second period.

3. The diagnosis supporting system according to claim 2, wherein the processing circuitry is further configured to calculate the second change amount based on a vector indicating the intervention information in the first period and a vector indicating the intervention information in the second period.

4. The diagnosis supporting system according to claim 2, wherein the processing circuitry is further configured to calculate the first change amount based on a condition of the patient based on the patient information in the first period, and based on a condition of the patient based on the patient information in the second period.

5. The diagnosis supporting system according to claim 1, wherein the processing circuitry is further configured to perform display based on the first change amount and the second change amount by using a mixed color in which two colors are mixed according to the ratio between the first change amount and the second change amount.

6. The diagnosis supporting system according to claim 5, wherein the processing circuitry is further configured to perform chronological display based on at least one of the patient information and the intervention information, and indicate the change point by using the mixed color.

7. The diagnosis supporting system of claim 1, wherein the processing circuitry is further configured to sequentially display a different one of the first change amount, the second change amount, the patient information, and the intervention information in response to sequential selection of the icon by the user.

8. The diagnostic supporting system of claim 1, wherein the processing circuitry is further configured to display, as the icon, a bar having a color determined by the ratio.

9. A diagnosis supporting system, comprising:
a memory that stores medical information including patient information relating to a medical condition of a patient, and intervention information relating to a medical intervention for the patient; and
processing circuitry configured to
extract a change point in the stored medical information,
calculate a first change amount indicating a change in the patient information between before and after the change point, and a second change amount indicating a change in the intervention information between before and after the change point, and
perform display of at least one of the patient information and the intervention information based on the calculated first change amount and the calculated second change amount in a display mode set by the processing circuitry according to at least one of the calculated first change amount and the calculated second change amount, so as to display the first change amount and the second change amount in an order set according to at least one of the calculated first change amount and the calculated second change amount, wherein the processing circuitry is further configured to display an icon representing the extracted change point, and display one of the first change amount, the second change amount, the patient information, and the intervention information adjacent to the icon, in response to selection of the icon by a user.

10. A diagnosis supporting apparatus, comprising:
processing circuitry configured to
extract a change point in stored medical information including patient information relating to a medical condition of a patient and intervention information relating to a medical intervention for the patient,
calculate a first change amount indicating a change in the patient information between before and after the change point, and a second change amount indicating a change in the intervention information between before and after the change point, and
perform display of at least one of the patient information and the intervention information based on the calculated first change amount and the calculated second change amount in a display mode set by the processing circuitry according to a ratio between the calculated first change amount and the calculated second change amount, so as to visually indicate a relationship between the first and second change amounts, wherein the processing circuitry is further configured to display an icon representing the extracted change point, and display one of the first change amount, the second change amount, the patient information, and the intervention information adjacent to the icon, in response to selection of the icon by a user.

11. A diagnosis supporting method, comprising:
extracting a change point in stored medical information including patient information relating to a medical condition of a patient and intervention information relating to a medical intervention for the patient;
calculating a first change amount indicating a change in the patient information between before and after the change point, and a second change amount indicating a change in the intervention information between before and after the change point; and
performing display of at least one of the patient information and the intervention information based on the calculated first change amount and the calculated second change amount in a display mode set according to a ratio between of the calculated first change amount and the calculated second change amount, so as to visually indicate a relationship between the first and second change amounts, wherein the method further includes displaying an icon representing the extracted change point, and displaying one of the first change amount, the second change amount, the patient information, and the intervention information adjacent to the icon, in response to selection of the icon is by a user.

12. A diagnosis supporting apparatus, comprising:
processing circuitry configured to extract a change point in stored medical information including patient information relating to a medical condition of a patient and intervention information relating to a medical intervention for the patient, calculate a first change amount indicating a change in the patient information between before and after the change point, and a second change amount indicating a change in the intervention information between before and after the change point, and perform display of at least one of the patient information and the intervention information based on the calculated first change amount and the calculated second change amount in a display mode set by the processing circuitry according to a ratio between the first change amount and the second change amount, so as to display the first change amount and the second change amount in an order set according to at least one of the calculated first change amount and the calculated second change amount, wherein the processing circuitry is further configured to display an icon representing the extracted change point, and display one of the first change amount, the second change amount, the patient information, and the intervention information adjacent to the icon, in response to selection of the icon by a user.

13. A diagnosis supporting method, comprising:

extracting a change point in stored medical information including patient information relating to a medical condition of a patient and intervention information relating to a medical intervention for the patient;

calculating a first change amount indicating a change in the patient information between before and after the change point, and a second change amount indicating a change in the intervention information between before and after the change point; and performing display of at least one of the patient information and the intervention information based on the calculated first change amount and the calculated second change amount in a display mode set according to a ratio between the first change amount and the second change amount, so as to display the first change amount and the second change amount in an order set according to at least one of the calculated first change amount and the calculated second change amount, wherein the method further includes displaying an icon representing the extracted change point, and displaying one of the first change amount, the second change amount, the patient information, and the intervention information adjacent to the icon, in response to selection of the icon is by a user, wherein the method further includes displaying an icon representing the extracted change point, and displaying one of the first change amount, the second change amount, the patient information, and the intervention information adjacent to the icon, in response to selection of the icon is by a user.

* * * * *